United States Patent [19]
Lindgren et al.

[11] Patent Number: 6,056,082
[45] Date of Patent: May 2, 2000

[54] ERGONOMIC BANDED EAR PLUG

[75] Inventors: Mats Ernst Gustav Lindgren; Lars Henrik Stigers, both of Vikmanshyttan, Sweden; Floyd L. Foslien, Troy, Wis.; Liana V. Palaikis, Woodbury, Minn.

[73] Assignee: 3M Innovative Properties Company, St. Paul, Minn.

[21] Appl. No.: 08/853,214

[22] Filed: May 9, 1997

[51] Int. Cl.$^7$ .................................................. H04R 25/02
[52] U.S. Cl. ............................................ 181/130; 128/864
[58] Field of Search ..................................... 181/130, 131, 181/135; 381/183, 187; 2/209; 128/864, 867

[56] References Cited

U.S. PATENT DOCUMENTS

| | | |
|---|---|---|
| Re. 29,487 | 12/1977 | Gardner, Jr. . |
| 1,225,422 | 5/1917 | Feher . |
| 2,782,423 | 2/1957 | Simon et al. . |
| 3,085,253 | 4/1963 | Ulrich et al. . |
| 3,295,631 | 1/1967 | Machlup . |
| 3,430,261 | 3/1969 | Benner . |
| 3,504,760 | 4/1970 | Littmann . |
| 3,505,684 | 4/1970 | Hutchinson et al. . |
| 3,547,219 | 12/1970 | Bothos . |
| 3,661,225 | 5/1972 | Anderson . |
| 3,845,505 | 11/1974 | Davison et al. . |
| 3,864,756 | 2/1975 | Desimone . |
| 3,895,627 | 7/1975 | Leight . |
| 3,934,674 | 1/1976 | Shore et al. ............................. 181/135 |
| 3,944,018 | 3/1976 | Satory . |
| 3,970,082 | 7/1976 | Leight . |
| 3,993,161 | 11/1976 | Shore ..................................... 181/135 |
| 4,069,512 | 1/1978 | Palmser . |
| 4,104,743 | 8/1978 | Bottger . |
| 4,347,631 | 9/1982 | Newcomb . |
| 4,461,290 | 7/1984 | Gardner, Jr. et al. . |
| 4,490,857 | 1/1985 | Leight et al. . |
| 4,615,050 | 10/1986 | Lönnstedt . |
| 4,671,265 | 6/1987 | Andersson . |
| 4,727,585 | 2/1988 | Flygstad . |
| 4,819,624 | 4/1989 | Leight et al. . |
| 4,867,149 | 9/1989 | Falco ....................................... 128/864 |
| 4,944,361 | 7/1990 | Lindgren et al. . |
| 5,068,923 | 12/1991 | Sjöqvist . |
| 5,609,164 | 3/1997 | Dyrud et al. . |
| 5,749,373 | 5/1998 | Dix ......................................... 128/864 |

FOREIGN PATENT DOCUMENTS

| | | |
|---|---|---|
| 0 587 925 A1 | 3/1994 | European Pat. Off. . |
| 0 587 925 B1 | 3/1994 | European Pat. Off. . |
| 0 836 841 A2 | 4/1998 | European Pat. Off. . |
| 452623 | 5/1913 | France . |
| 32 26 407 C2 | 1/1984 | Germany . |
| 296 11 562 U1 | 12/1996 | Germany . |
| 910149 | 3/1982 | Russian Federation . |
| WO 92/00049 | 1/1992 | WIPO . |

OTHER PUBLICATIONS

Product Literature: "Reflex™ Hearing Protection with a New Twist," Aearo Company, 1996.

*Primary Examiner*—Khanh Dang
*Attorney, Agent, or Firm*—James A. Rogers

[57] ABSTRACT

An ergonomic banded ear plug device includes a band having a connecting section and two legs configured for extending under the chin or behind the back of the head of the wearer. Plug retaining members are at the end of each of the legs for retaining resilient foam-type plug members that substantially block the ear canal of the wearer. In addition, each of the legs includes a resilient flexing section including a pair of parallel extending ribs with a slot formed therebetween. The ribs bendably flex outward and downward to provide a substantially constant force against the ear of the wearer over a broad range of sizes and rotatably flex for improved fit.

8 Claims, 9 Drawing Sheets

ERGONOMIC BANDED EAR PLUG

BACKGROUND

1. Field of the Invention

The present invention is directed to an ear plug apparatus having a band generally configured for extending under the neck or behind the head of the wearer, and in particular to an ergonomic banded ear plug device.

2. Prior Art

Devices for substantially blocking or covering the ear canal of the wearer to protect the wearer from excessive and damaging noise are well known. Muff type devices are known that cover the entire ear. However, muffs are large, often heavy and may be uncomfortable to wear. Moreover, muffs usually require a cumbersome support structure such as a helmet or a harness extending over the top of the head. Ear plug devices are also known that substantially block or cover each auditory canal. One type of an ear plug is inserted into the ear canal individually without being connected. These small plugs are easily misplaced and require care during insertion so that the plugs do not fall out, as there is no pressure to hold the plugs in place other than friction. Still other ear plug devices include a band that is deformed slightly to provide compressive force against the plug members to hold the plug members in position.

There are several challenges in blocking the ear canal to decrease noise entering the canal. Custom molded plugs may be used, but they require a special fitting and are very expensive. Other molded plugs may not fit the varied shapes of wearers' ears, causing discomfort and/or poor noise attenuation. Compressible resilient foam type plugs may also be used that are inserted into the ear canal and allowed to expand so that the friction between the individual plugs and the ear canal is sufficient to retain the plug member in the ear. Care should be taken to select proper materials for the plugs that will conform to the ear canal without causing excessive force against the ear canal for the wearer, while providing sufficient force to substantially block sound to the ear canal.

As the shape of each person's ears and the shape and orientation of each person's ear canal varies, substantially blocking the canal in a satisfactory manner is difficult. Known devices may insert into the ear and cover the canal, but do not always provide a satisfactory fit. Usually, the entrances of human ear canals have an overall tendency to extend slightly upward and forward rather than transverse to the center plane of the wearer, but the precise orientation varies from person to person. Prior banded devices typically exert force directly inward against ear plug members within the same plane as the band and do not provide for positioning the plug members within a range of orientations to substantially match the range of human ear canal entry angles. Incorrect orientation of the plug members in a banded plug configuration leads to a poor fit with the entrance of the human ear canal. When this occurs, the plug is less effective at blocking noise and/or less comfortable to wear.

Banded ear plug devices typically extend outward in a substantially U-shaped configuration with the plug members' normal separation distance often less than the width of the wearer's neck. The legs of the band are pulled apart to fit the plugs over the wearer's ears. Since the bands are pulled outward from their normal position, the bands exert an inward force against the ear plug members, retaining them against the ears. Although prior devices are able to widen to various head sizes, the force exerted usually varies as the separation distance increases. This creates problems that are exacerbated by varying head sizes as the force exerted against the wearer's ears may be too little for smaller head sizes and too great for larger head sizes. The banded ear plug devices may not have sufficient force against the ear plug members for satisfactory sound attenuation for some wearers, while other wearers may experience discomfort from excessive force exerted on the ear plugs and to the ears.

It can be seen then that a new and improved banded ear plug device is needed. Such a device should provide for substantially covering the ear canal of the wearer in a comfortable manner. Such a device should provide for adapting to a wide variety of head sizes with both a vertical and horizontal range of engagement orientations for covering typical ear canals. Such a device should provide substantially constant force against the ears over a range of wearers' head sizes. The device should fit comfortably under the wearer's chin or behind the back of the wearer's head and should be light weight enough so that the device can be worn for extended periods of time without discomfort. The present invention addresses these as well as other problems associated with band type ear plug devices.

SUMMARY OF THE INVENTION

The present invention is directed to a banded ear plug device, and in particular to an ergonomic band device supporting ear plugs and providing an improved fit across a wide range of sizes. An ergonomic banded ear plug includes plug retaining members that extend inward toward one another. When worn, the retaining members may extend slightly upward in an orientation that provides a more comfortable fit for the wearer. In addition, the upward angle retains the plugs at a position that more effectively blocks the ear canal to reduce the noise transmitted into the ear canal.

The band includes a center connecting section generally configured for extending under the chin or behind the head or neck of the wearer to two end sections. Between the end portions and connecting section are flexing sections. Each of the flexing sections include a pair of ribs extending substantially parallel to one another with a slot or connecting membrane formed therebetween. The ribs are oriented at an angle along their length in a v-shaped cross-sectional configuration rather than substantially co-planar. The ribs have a much thinner cross-section than the end sections or the connecting section. The ribs permit rotational and bending flexure of the band and restrict substantially all of the flexure within the flexing sections. The ribs also taper slightly from the connecting section to the end sections in a preferred embodiment. When bent, the ribs twist slightly at their middle to a substantially co-planar configuration. This arrangement provides for substantially constant force against the plug members and ears across the normal range of flexure to fit the various head sizes. The flexing sections also rotatably flex along their length so the retaining members supporting the ear plugs may be rotated out of the plane of the band for improved fit.

These features of novelty and various other advantages which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

Referring now to the drawings, wherein like reference letters and numerals indicate corresponding structure throughout the several views.

DETAILED DESCRIPTION OF THE PREFERRED EMBODIMENT

Figure 1:
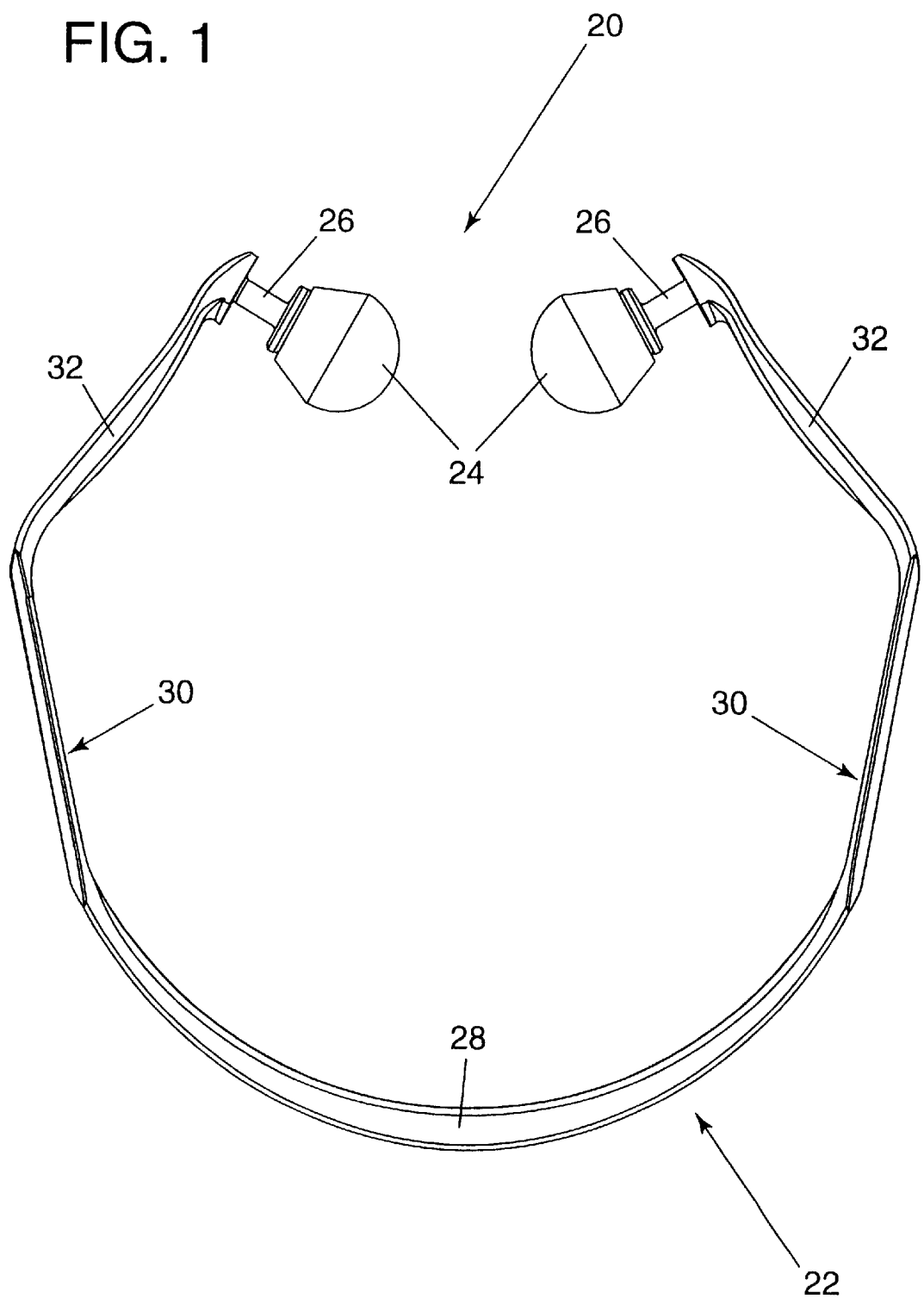
FIG. 1 shows a front elevational view of a ear plug device according to the principles of the present invention.

Referring now to the drawings, and in particular to FIG. 1, there is shown a banded ear plug device, generally designated 20. The banded ear plug device 20 includes a band 22 supporting plug members 24 which insert into or over the auditory canals of a wearer. The band 22 is preferably a monolithic, lightweight, break resistant plastic member. However, the band 22 could be made of separate elements and/or of several materials. The band 22 is typically made from thermoplastic polymers such as polyester, polypropylene, polyethylene, polyamide, polyacetal, ABS resins or other thermoplastics. A preferred material is Delrin™ 511P by Dupont, selected for its low creep and good spring characteristics. The band 22 is made by any of several well known molding techniques such as injection molding, compression molding or transfer molding. The band 22 includes a center connecting section 28 configured for extending along the sides of the head and comfortably under the chin or behind the back of the head or neck of a wearer while the plug members 24 are covering the ear canals. When dropped down, the connecting section 28 should be worn without applying any tension against the chin or neck of the wearer. At each end of the connecting section 28 are flexing sections 30 that bendably flex outward and rotatably flex to orient the plug members 24 to fit at the proper position for substantially blocking or covering the ear canals of each wearer. The flexing sections 30 provide a range to optimize the fit to different size heads. End sections 32 adjacent the flexing sections 30 include retainer studs 26. The studs 26 angle slightly downward within the plane of the band 22 in a non-flexed band position, but angle slightly up when flexed, as explained hereinafter. Each stud 26 inserts into and retains a plug member 24. Although the plug members 24 are usually removable, replaceable members, they may be integrally formed with the band 22 for some uses. When dropped down and in a non-flexed position, the ear plug device 20 may be retained by the studs 26 or the connecting section 28 resting around the back of the neck of the wearer.

Figure 2:
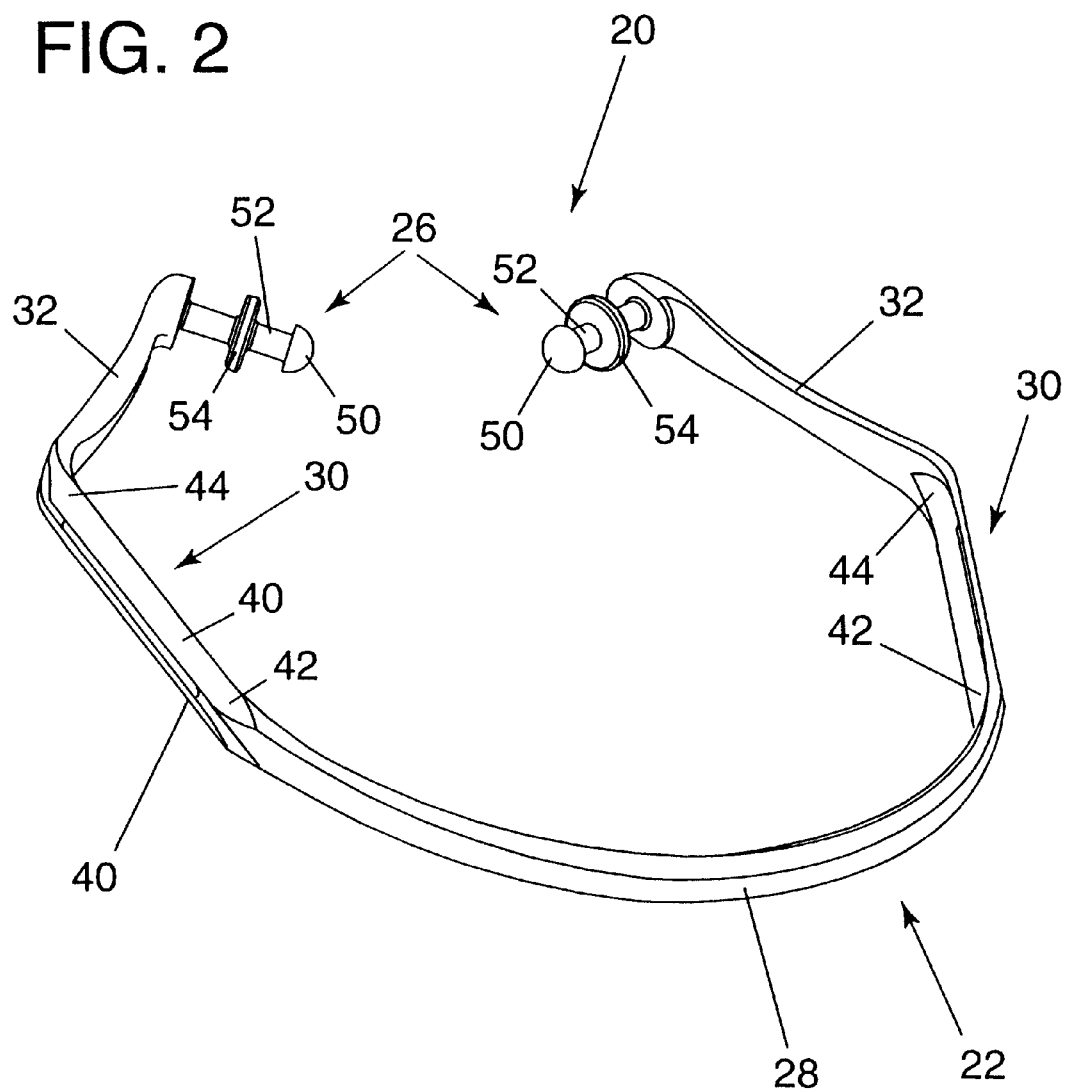
FIG. 2 shows a perspective view of the ear plug device shown in FIG. 1 with the plug members removed.
Figure 3:
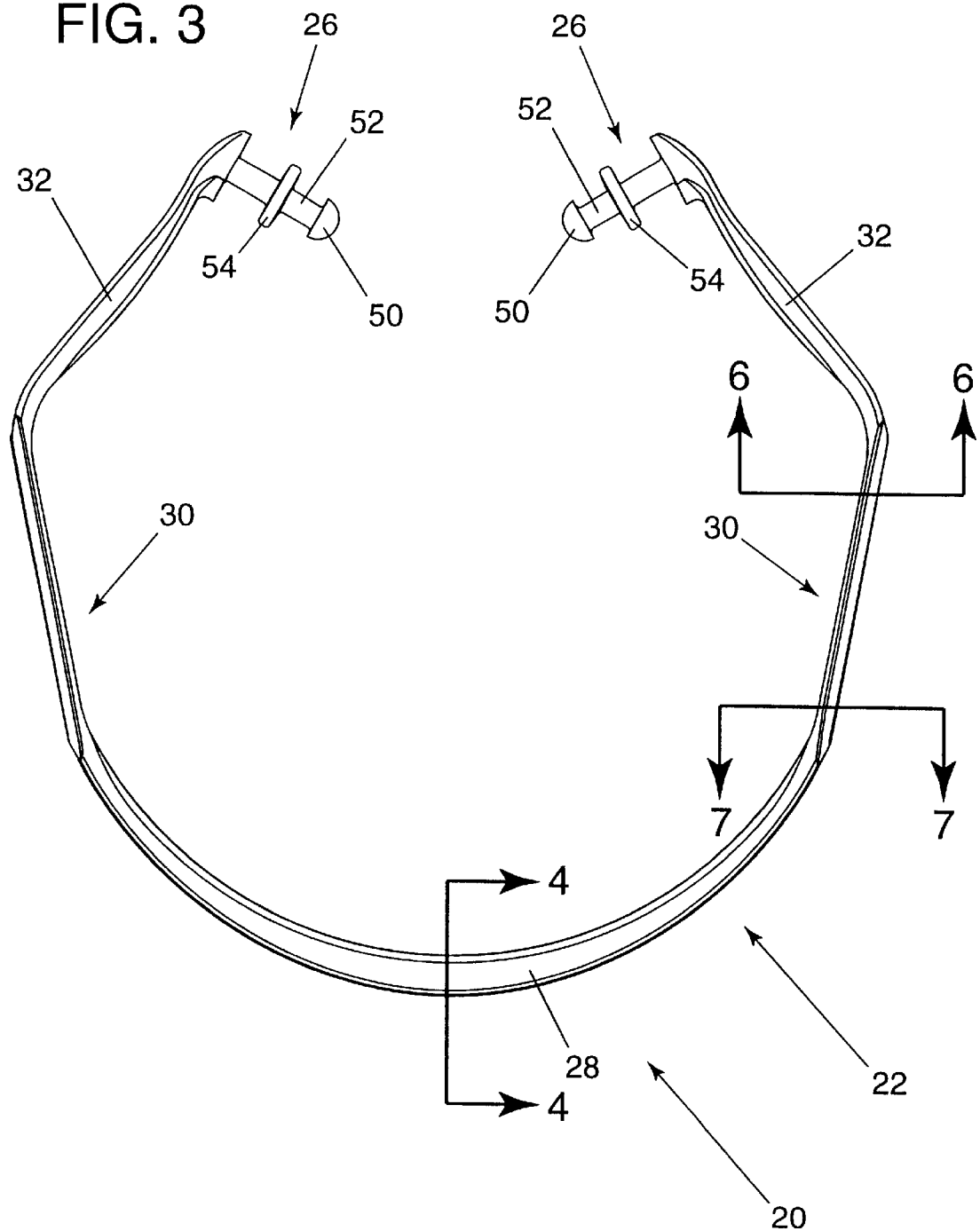
FIG. 3 shows a front elevational view of the ear plug device shown in FIG. 2.

Referring now to FIGS. 2 and 3, the studs 26 have a neck portion 50 extending inward from the end sections 32. At the end of the neck portion 52 is a hemispherical portion 50. In addition, extending radially outward from the neck portion 52 and spaced apart from the hemispherical portion 50 is a flange 54. The hemispherical portion 50 and neck portion 52 are configured to retain and orient various designs of compressible resilient ear plug members, as explained hereinafter. The flange 54 has a dimension greater than the width of a typical human ear canal. The flange 54 prevents the stud 26 from being inserted too far into the ear canal and injuring the wearer.

Figure 4:
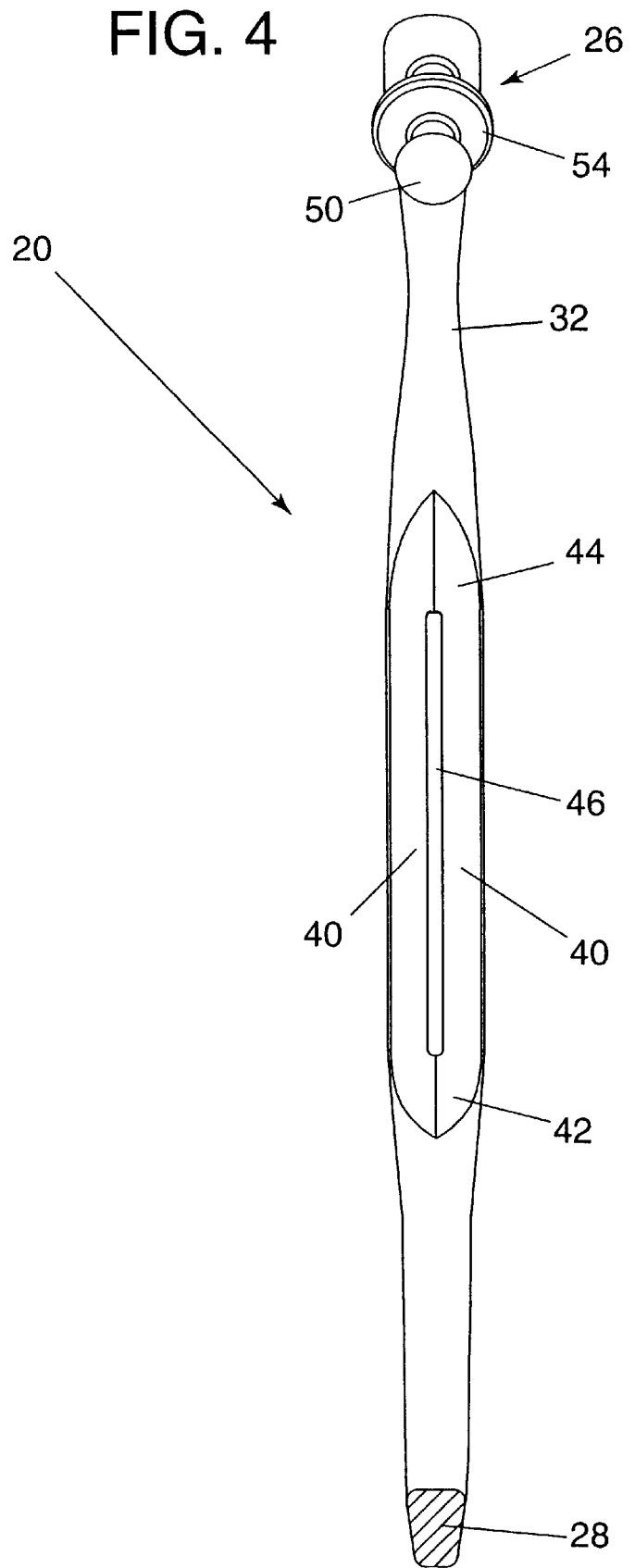
FIG. 4 shows a side sectional view of the ear plug device taken along line 4—4 in FIG. 2.
Figure 6:
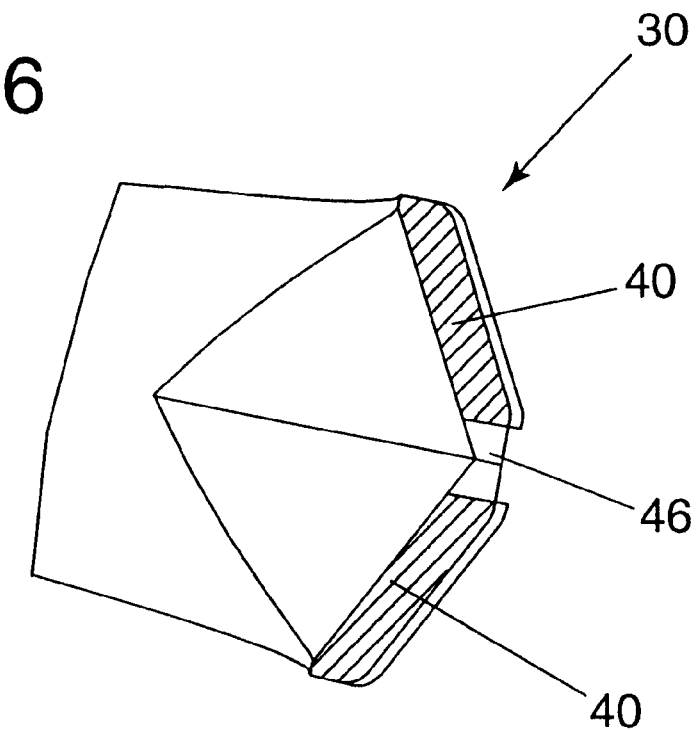
FIG. 6 shows a sectional view taken along line 6—6 of FIG. 3.
Figure 7:
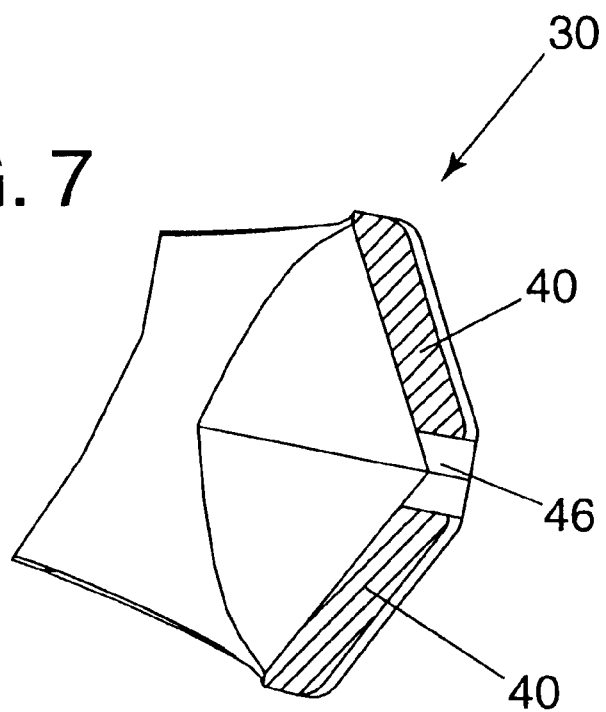
FIG. 7 shows a sectional view taken along line 7—7 of FIG. 3.

Referring now to FIGS. 2, 3 and 4, the flexing section 30 is shown more clearly. Each flexing section 30 includes a pair of ribs 40 extending between the end section 32 and the center connecting section 28 and form a slot 46 therebetween. Although an open slot 46 is shown, it can be appreciated that a thin connecting membrane or spaced apart cross members that do not limit relative movement or flexure of the ribs 40 may also be located intermediate the ribs 40. The ribs 40 are thin planar members having a thinner cross-section than the connecting sections 28 or the end sections 32. The ribs 40 bend to flex outward as well as rotatably flex. The ribs 40 run substantially parallel to one another, but extend at an angle to one another along their length, as shown in FIGS. 6 and 7. As explained hereinafter, the ribs 40 provide for both bending flexure, as shown in FIG. 5, and rotational flexure, as shown in FIG. 8.

Referring again to FIGS. 2–5, the ribs 40 taper from a first end 42 to a second end 44. In the embodiment shown, the ribs taper from a thickness of 1.1 mm to 0.9 mm, as best shown in FIGS. 6 and 7. However, other materials and different applications may require a differing taper or no taper. Thickness of the ribs 40 may vary from about 0.5 mm up to about 2.0 mm, depending on the application and band materials. The tapering cross section of the ribs 40 along with the slot 46 and the angled relative orientation reduces stress and strain when flexed and provides for maintaining a substantially constant force directed toward the plug members 24 and the ears across the range of bending and rotational flexure. It can be appreciated that in a bent flexed position, as shown in FIG. 5, the ribs 40 twist and flatten out to extend substantially co-planar at their middle to provide flexure outward.

Figure 8:
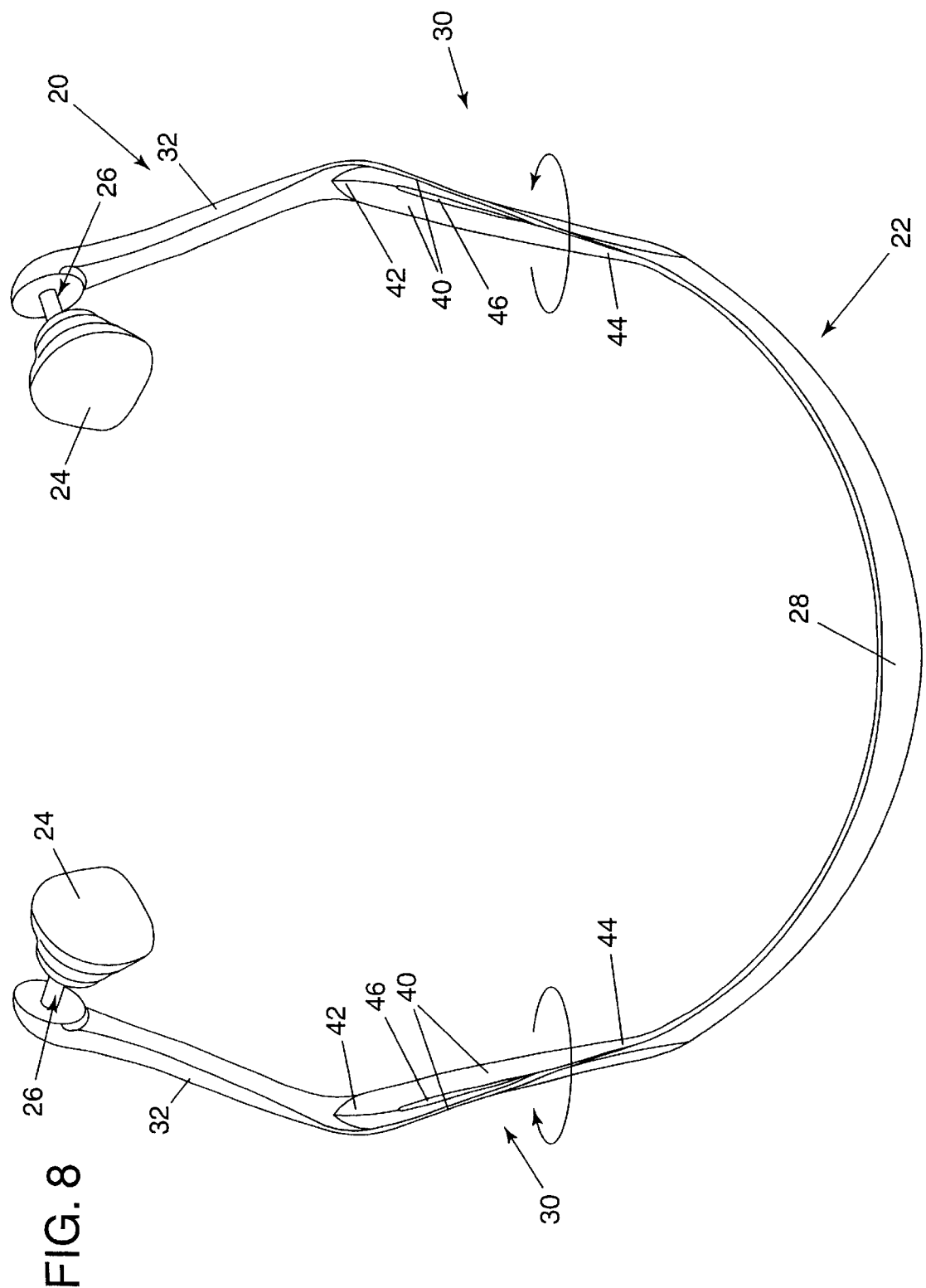
FIG. 8 shows a front elevational view of the ear plug device shown in FIG. 1 in a rotationally flexed position.

In addition to bendably flexing outward, the ribs 40 coordinate to flex rotatably so that the end sections 32 may be rotated out of the plane of the band 22, as shown in FIG. 8. This rotating action provides for optimizing the angle at which the plug members 24 engage the associated ear canals of the wearer. It can further be appreciated that the center connecting section 28 and the end sections 32 have a much thicker cross section than the flexing sections 30 and are substantially more rigid. Therefore, substantially all of the flexure, both bending and rotating, is limited to the flexure of the flexing sections 30. It can also be appreciated that the ribs 40 can bendably flex and rotatably flex at the same time.

Figure 5:
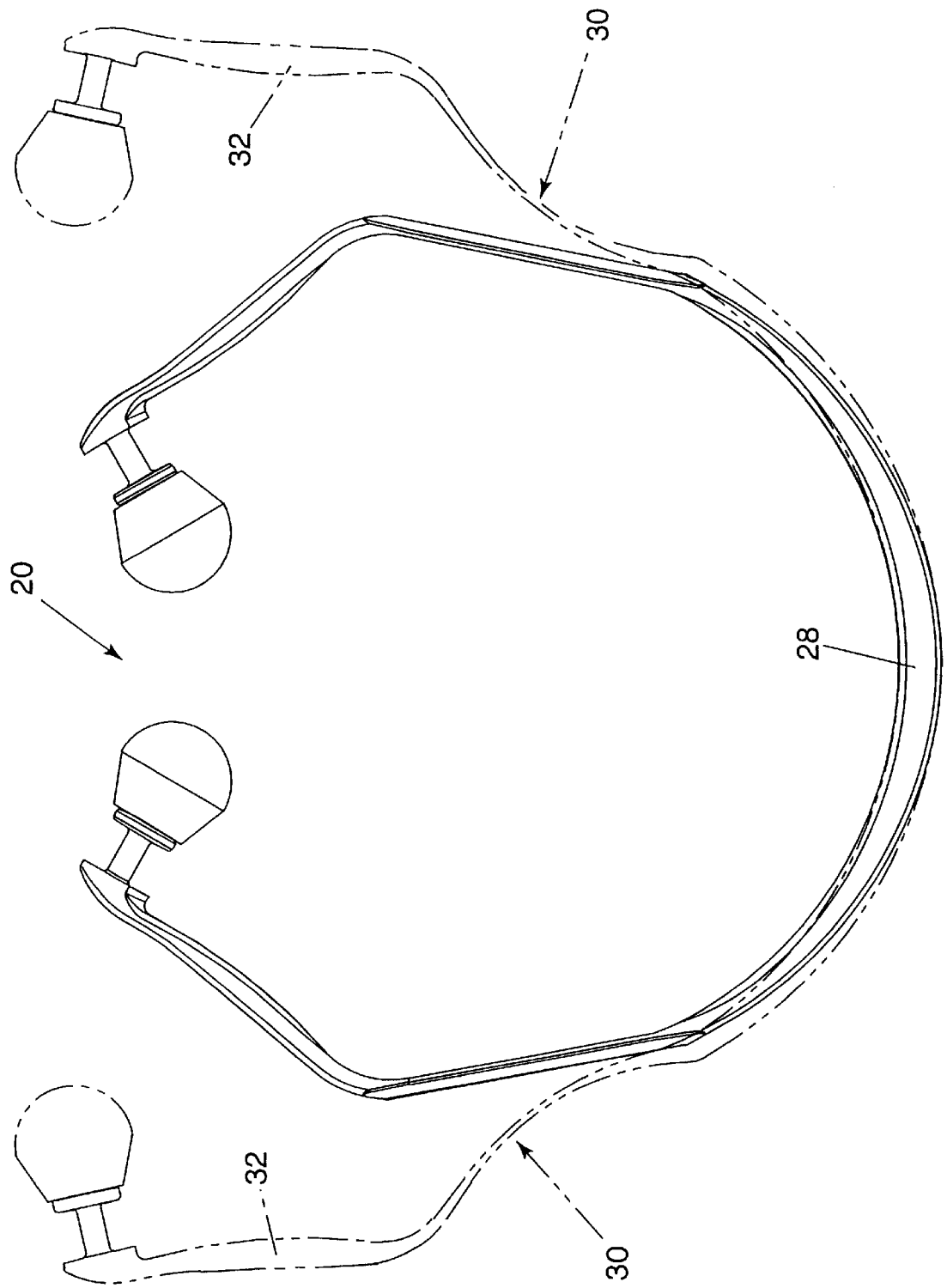
FIG. 5 shows a front elevational view of the ear plug device shown in FIG. 2 and in a bent flexed position shown in phantom.

As shown in FIG. 5, the vertical distance between the connecting section 28 and the studs 26 increases as the ribs 40 flex outward and the studs move outward and upward. The ear plug device 20 may be worn in several positions, but is sized so that the connecting section 28 may extend comfortably under the chin or behind the head and neck of the wearer, even when bendably flexed.

Figure 12:
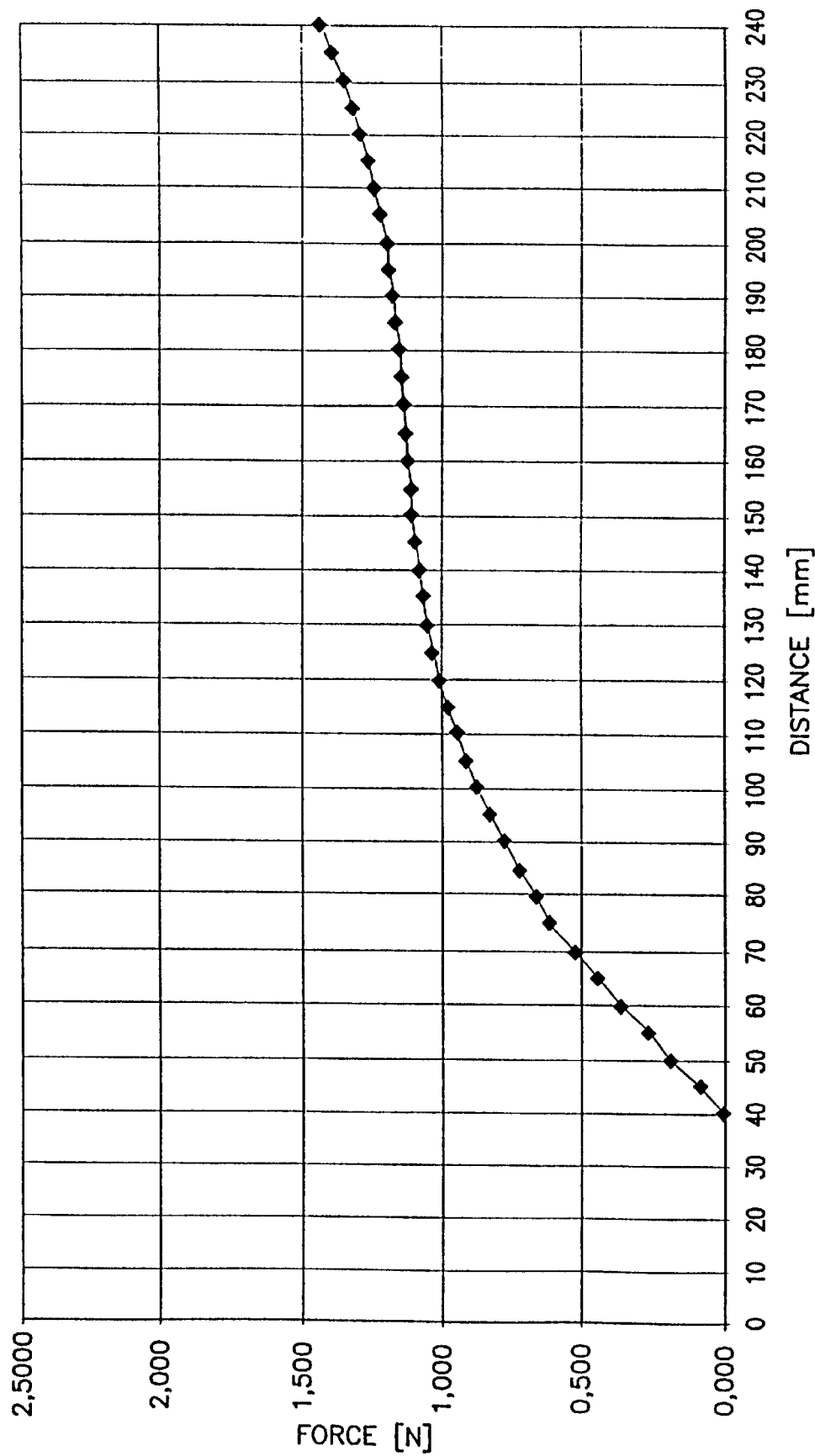

Referring now to FIG. 12, it can be seen that the force is substantially constant in the normal bendably flexing range of the ribs 40. For most wearers, the ribs 40 are flexibly bent so that the distance between the studs 26 is about 100 millimeters to typically no more than about 170 millimeters. The ribs 40 provide force leveling so that the force exerted is maintained at more than 0.7 Newtons and less that 1.3 Newtons and for most wearers is between 0.9 and 1.1 Newtons. This is sufficient force to press the ear plug members 24 against the ears to substantially block the ear canal, without causing discomfort for the wearer. It can be seen that the design of the flexing sections 30 keeps the force within this desired range and substantially constant across the normal range of flexure. This provides for substantially constant force between various head sizes and a more comfortable fit for more wearers. Those skilled in the art can appreciate that by changing the material of the band 22, the length, thickness, width, relative angle and/or taper of the ribs 40, the force values shown in FIG. 12 may be varied. Moreover, as comfort level and noise attenuation performance required for various uses may change, greater or lesser force may be preferred.

Figure 9:
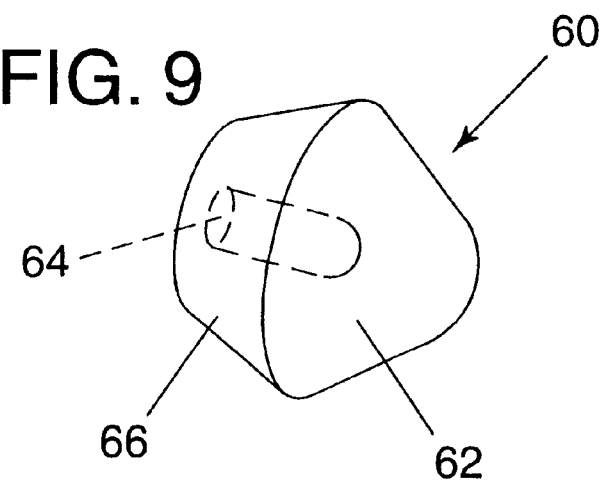
FIG. 9 shows a perspective view of a first embodiment of a plug member for use with the ear plug device shown in FIG. 1.
Figure 10:
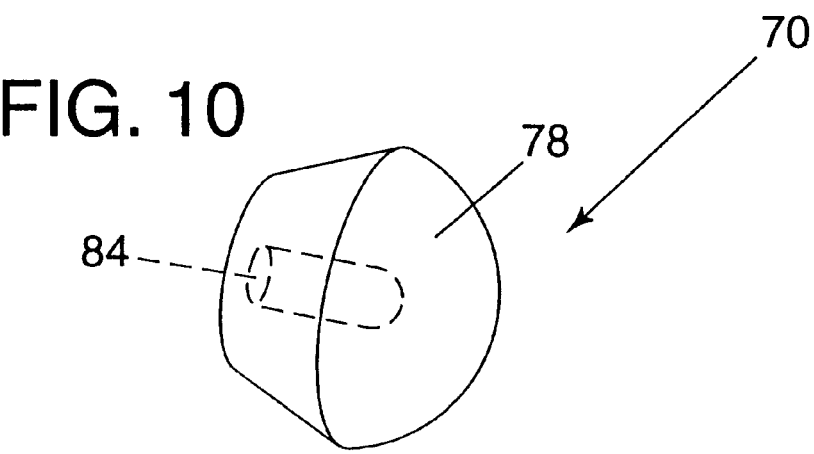
FIG. 10 shows a perspective view of a second embodiment of a plug member for use with the ear plug device shown in FIG. 1.
Figure 11:
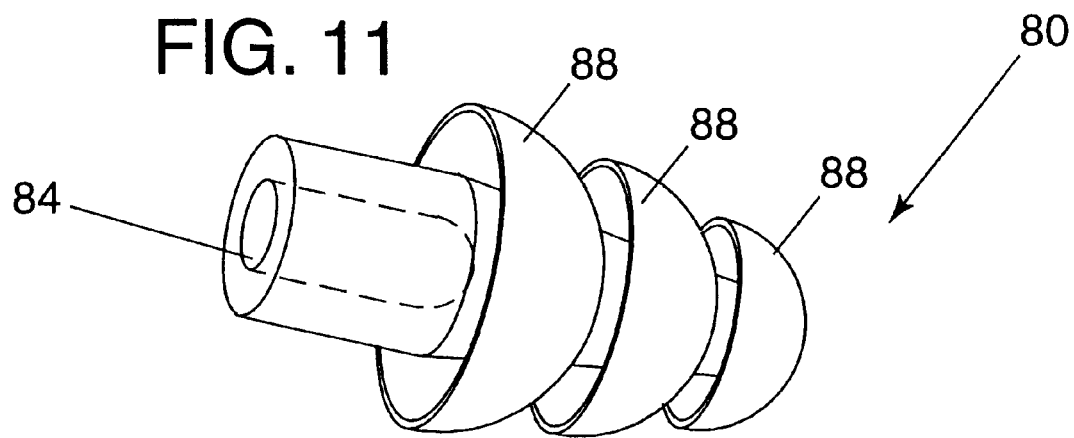
FIG. 11 shows a perspective view of a third embodiment of a plug member for use with the ear plug device shown in FIG. 1; and, FIG. 12 shows a graph of the pressure exerted by the plug members versus the distance flexed.

Referring to FIGS. 9–11, there are shown embodiments of ear plug members 60, 70, 80 for the banded ear plug device 20 of the present invention. Each of the embodiments 60, 70, 80 are formed of a compressible foam type material or an elastic deformable molded material. Such materials have sufficient resiliency to mold to the shape of the opening of the ear canal and to expand for substantially closing off the opening and reducing noise reaching the ear drum.

Referring in particular now to FIG. 8, a first embodiment of a plug member 60 includes a bore 64 extending partially through the plug. The end of the plug member 60 includes tapered sides 62 forming a frusto-conical end portion. The plug member 60 is preferably made of a compressible open cell foam type material that can be deformed against the opening to the ear canal of the wearer. The bore 64 is configured to fit over the hemispherical portion 50 of the stud 26 and constrict around the neck portion 52, as shown in FIG. 1. The constriction of the bore 64 at the neck portion 52 retains the plug member 60 on the stud 26.

Referring now to FIG. 10, there is shown a second embodiment of a plug member 70. The plug member 70 includes a bore 74 formed partially through the plug member 70 that constricts to fit over the hemispherical portion 50 of the stud 26 and constrict around the neck portion 52 as explained above. The plug 70 includes an arcing rounded end portion 78 configured for fitting partially into and covering the opening to the ear canal of the wearer.

Referring now to FIG. 11, there is shown a third embodiment of a plug member 80 of an elastic deformable molded material. The plug member 80 includes a bore 84 formed partially through the plug member 80. The plug member 80 is configured to extend to fit over the hemispherical portion 50 of the stud 26 and constrict around the neck portion 52 of the stud 26 to retain the plug member 80 on the stud 26, as explained above. The plug member 80 includes a plurality of hemispherical flanges 88 aligned in a stacked configuration extending outward from the bore 84. The plug member 80 is configured to extend substantially into the ear canal with the flanges 88 conforming to substantially close off the ear canal to sound waves. The flanges 88 increase in diameter from the end most flange toward the bore 84 and have an arcing hemispherical surface facing the insertion end of the plug 80 with a planar opposite surface to provide slight resistance to removal of the plug 80. The flanges 88 provide multiple blocking locations within the ear canal for improved noise attenuation.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An apparatus for supporting ear plugs, comprising:
   a band including a connecting section and two legs, said band configured for extending under the chin or behind the back of the head of a wearer;
   a plug retaining member at the end of each of the legs, said plug retaining member configured to retain ear plugs, wherein each plug retaining member extends inward toward the other;
   wherein each of said legs includes a resilient flexing section comprising at least two ribs having a slot therebetween wherein said ribs (i) have a first end and a second end, (ii) taper from said first end to said second end, and (iii) are angled at a v-shaped cross-sectional configuration;
   wherein, in use, the ribs are capable of twisting and flattening out to exert a substantially constant force across a range of bending flexure.

2. The apparatus of claim 1 further comprising two ear plugs.

3. The apparatus of claim 2, wherein the flexing sections exert a force of about 0.7 Newtons to about 1.3 Newtons across a range of bonding flexure.

4. An apparatus according to claim 2, wherein each of the ear plugs comprises a compliant open cell foam material.

5. An apparatus according to claim 4, wherein each of the plugs comprises a tapered end portion and tapered base forming a widened portion intermediate the end portion and the base portion.

6. An apparatus according to claim 2, wherein each of the plugs comprises a plurality of axially aligned stacked hemispherical flanges.

7. An apparatus according to claim 1, wherein the ribs taper between a thickness of 2.0 mm and 0.5 mm.

8. An apparatus according to claim 1 wherein the ribs bendably flex and rotatably flex.

\* \* \* \* \*